(12) United States Patent
Friesen et al.

(10) Patent No.: US 9,649,215 B2
(45) Date of Patent: May 16, 2017

(54) CONNECTING ELEMENT FOR ORTHOPEDIC COMPONENTS

(75) Inventors: Jeff Friesen, Salt Lake City, UT (US); Roland Auberger, Vienna (AT)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 454 days.

(21) Appl. No.: 12/992,012

(22) PCT Filed: May 20, 2009

(86) PCT No.: PCT/DE2009/000733
§ 371 (c)(1),
(2), (4) Date: Nov. 10, 2010

(87) PCT Pub. No.: WO2009/140955
PCT Pub. Date: Nov. 26, 2009

(65) Prior Publication Data
US 2011/0066255 A1    Mar. 17, 2011

(30) Foreign Application Priority Data

May 20, 2008   (DE) .................. 10 2008 024 750

(51) Int. Cl.
*A61F 5/01*     (2006.01)
(52) U.S. Cl.
CPC .................. *A61F 5/0102* (2013.01)
(58) Field of Classification Search
CPC ........ A61F 5/01; A61F 5/0102; A61F 5/0123; A61F 5/0125
USPC .............................. 602/5, 23, 26–28; 73/760
See application file for complete search history.

(56) References Cited

U.S. PATENT DOCUMENTS

| | | | |
|---|---|---|---|
| 4,104,605 A * | 8/1978 | Boudreaux et al. | 338/2 |
| 4,816,200 A * | 3/1989 | Stecher et al. | 264/610 |
| 5,088,479 A | 2/1992 | Detoro | |
| 5,591,261 A * | 1/1997 | Ciaramita | 118/13 |
| 6,876,134 B2 * | 4/2005 | Ikeda et al. | 310/330 |
| 6,888,194 B2 * | 5/2005 | Yoshino | 257/324 |
| 7,056,297 B2 * | 6/2006 | Dohno et al. | 601/48 |
| 7,416,537 B1 * | 8/2008 | Stark et al. | 602/16 |
| 7,462,160 B2 | 12/2008 | Nobbe et al. | |
| 7,578,799 B2 | 8/2009 | Thorsteinsson et al. | |
| 2003/0083596 A1 * | 5/2003 | Kramer | A61B 5/1071 600/595 |

(Continued)

FOREIGN PATENT DOCUMENTS

DE     3444628 A1    6/1986
DE     4205790 A1    9/1993

(Continued)

OTHER PUBLICATIONS

PCT International Search Report mailed Oct. 27, 2009 for PCT International Patent Application No. PCT/DE2009/000733.

*Primary Examiner* — Alireza Nia
*Assistant Examiner* — Camtu Nguyen
(74) *Attorney, Agent, or Firm* — Holland & Hart LLP

(57) ABSTRACT

The invention relates to a connecting element (5) between two orthopedic components, in particular prosthesis or orthosis components, which are rigidly coupled to one another and comprise a top part (2) and a bottom part (8). The connecting element (5) has a laminar structure, and at least one sensor (20) is arranged in the connecting element (5) in order to determine an effective moment or an effective force.

23 Claims, 2 Drawing Sheets

(56) References Cited

U.S. PATENT DOCUMENTS

| | | |
|---|---|---|
| 2004/0225242 A1 | 11/2004 | Lidolt et al. |
| 2006/0195197 A1* | 8/2006 | Clausen et al. .................. 623/24 |
| 2007/0027421 A1 | 2/2007 | Nobbe et al. |
| 2008/0039756 A1 | 2/2008 | Thorsteinsson et al. |

FOREIGN PATENT DOCUMENTS

| | | |
|---|---|---|
| DE | 9319050.6 U1 | 12/1993 |
| DE | 10311189 A1 | 10/2004 |
| DE | 102004027252 A1 | 12/2005 |
| DE | 102004030570 A1 | 1/2006 |
| EP | 1714623 A2 | 10/2006 |
| GB | 2168488 A | 6/1986 |
| RU | 94042368 A1 | 9/1996 |
| RU | 95110131 A1 | 6/1997 |
| RU | 95107193 A | 11/1997 |
| RU | 2277395 C1 | 6/2006 |
| WO | 2005058211 A2 | 6/2005 |
| WO | 2006053283 A2 | 5/2006 |

\* cited by examiner

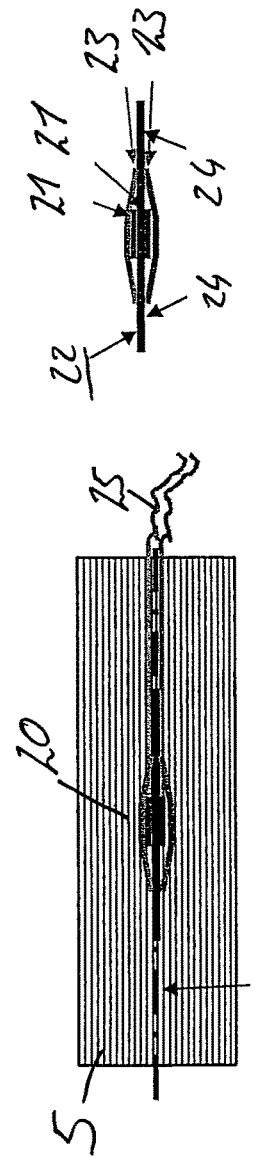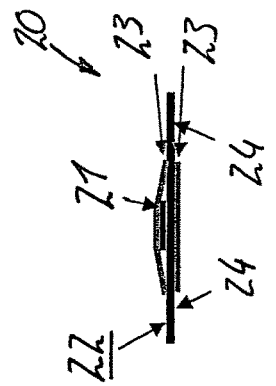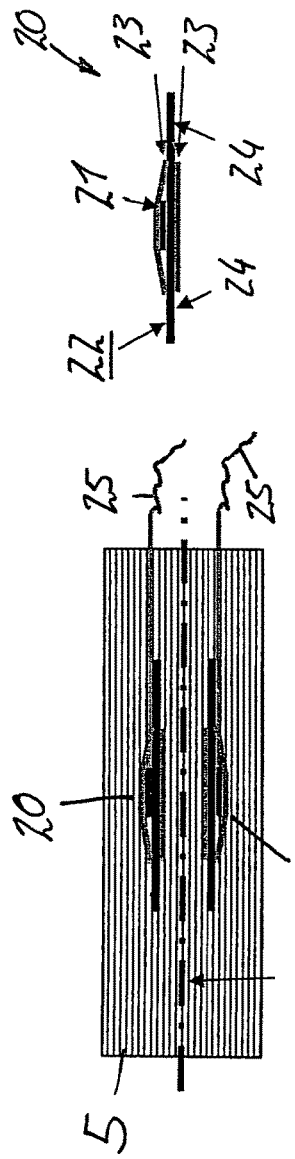

CONNECTING ELEMENT FOR ORTHOPEDIC COMPONENTS

The invention relates to a connecting element between two rigidly coupled orthopedic components, in particular orthosis or prosthesis components, with an upper part and a lower part. A rigid connection is present when no pivoting is possible about a fixed pivot axis. The rigid connection is also obtained when the connecting element is mounted resiliently in a holder. A rigid connection does not preclude an elastic configuration of the connecting element, in particular a bending elasticity. Such a connecting element is particularly suitable for use in what is called a knee-ankle-foot orthosis and serves to connect a foot part to a lower-leg structure, which is arranged securely on the lower leg of an orthosis wearer. Such an orthosis serves to support the apparatus of locomotion. The invention also relates to an orthosis device having such a connecting element.

U.S. 2008/0039756 A1 discloses an orthosis with a frame, of which the proximal frame part can be fastened to the thigh of an orthosis wearer. A distal frame part is mounted pivotably on the proximal frame part via a knee joint. A foot part is secured in an articulated manner on the distal end of the distal frame part. The foot part can be driven and pivoted via an actuator. The proximal frame part can be moved relative to the distal frame part via a knee actuator. Such an orthosis serves to actively support controlled movement.

WO 2005/058211 A2 describes an orthosis of the type in question with medially and laterally arranged struts, which are connected to each other via a knee joint. The struts are maintained at a defined distance from each other by cuffs, on which the medial and lateral struts are secured. At the distal end of the thigh part and at the proximal end of the lower part, the cuffs are designed such that they form a holder for a hydraulic cylinder. The hydraulic cylinder is arranged dorsally when the orthosis is being worn. A disadvantage of this is that the damper device takes up a lot of space and cannot generally be worn under normal trousers.

The use of a beam spring made of a fiber-reinforced composite material is known, for example, in association with a foot lifting orthosis from DE 10 2004 027 252.2. Fastening means for securing the spring to the foot and to the lower leg are arranged on the curved beam spring.

The object of the present invention is to make available a connecting element, particularly for orthosis devices or prosthesis devices, with which improved detection of effective forces between the connected components is achieved. According to the invention, this object is achieved by a connecting element having the features of the main claim. Advantageous embodiments and developments of the invention are set forth in the dependent claims.

The connecting element according to the invention between two rigidly coupled orthopedic components with an upper part and a lower part is characterized in that the connecting element has a laminate structure, and at least one sensor for determining an effective moment or effective forces is arranged in the connecting element. The sensor or the sensors can be used to determine the instantaneous effective moment, e.g. torsional moment or bending moment, from which conclusions can be drawn regarding the instantaneous load on the structure or, for example, the instantaneous gait phase. A rigid connection is present when the upper part and the lower part are not connected to each other in an articulated manner.

The sensor system for determining the forces or moments is preferably laminated inside the connecting element, i.e. surrounded by the laminate layers, such that the sensor is substantially screened off from external influences and determines only the effective forces and moments inside the connecting element. The same applies to a laminated-in signal-conditioning or amplifying circuit, which is preferably located near the sensor system.

In order to minimize disturbances resulting from the laminated-in state, a development of the invention entails that each sensor is screened off from undesired shearing forces of the laminate material, and this is preferably achieved by the fact that a separating layer, in particular a film or a heat-shrink sleeve, is arranged between the sensor and the laminate material. This ensures that shearing forces inside the laminate material during bending of the connecting element are not transmitted to the sensor, which could render the measurement incorrect. The separating layer can be arranged on one side of the sensor and screen only one side of the sensor from shearing forces.

The sensor is preferably designed as a strain gauge arrangement, which is arranged on a substrate, and the substrate is also preferably laminated in the connecting element. The substrate is in particular laminated in the connecting element in such a way that the substrate follows the deformations of the connecting element, with the result that conclusions about the loading of the connecting element can be drawn from the deformation of the substrate. In this way, a module is made available which is composed of the substrate and of a strain gauge applied previously to the latter, if appropriate together with a circuit for evaluating, conditioning and amplifying the sensor signal. This module can be easily laminated into the connecting element during production of the latter, in which case connectors for transmitting the sensor data have to be routed out from the connecting element, for example in the form of cables or laminated-in plug bushings. The sensor data can also be transmitted wirelessly, e.g. via an inductive coupling or radio. For radio transmission, the use of strain gauges based on SAW (surface acoustic wave) technology is advantageous in particular. These strain gauges can be interrogated wirelessly, their measurement principle being based on the fact that the speed of propagation of an acoustic surface wave in a crystal, and therefore the signal propagation time, is dependent on the state of mechanical stress thereof.

The sensor unit as a whole can be configured on a single circuit board, on which the evaluation electronics are also located. Provision is in this case made that the sensor, for example a strain gauge, is applied to the circuit board by means of thick-film technology. In this way, no separate substrate material is required, such that overall a compact structure can be obtained. The circuit board thus serves as substrate of the sensor and of the integrated circuitry of the evaluation electronics. If appropriate after evaluation by the evaluation electronics, the data from the sensor are transmitted to a control device, which is connected to the sensor. The control device can likewise be arranged on the circuit board. The control device is coupled to an actuator, such that the behavior of the actuator can be changed, i.e. varied, on the basis of the sensor data.

The separating layer can be secured on the substrate such that an encapsulated sensor can be incorporated into the laminate material without the need for further work steps. The separating layer, designed as a film for example, can be bonded to the substrate, such that only the bending forces or bending moments transmitted to the substrate are measured by the sensor. Instead of a film, a heat-shrink sleeve can also be used. In a development of the invention, the sensor and, if appropriate, the substrate are arranged floating in the connecting element, in order to avoid a situation where, for example in the event of a thermally induced expansion of the substrate during use, the substrate is itself deformed when the laminate material does not expand to the same extent. This would be the case, for example, if fiber-reinforced composite materials were paired with a metal substrate. A floating arrangement avoids, on the one hand, the generation of an incorrect signal and, on the other hand, a bursting of the encapsulating material of the connecting element.

The substrate and therefore also the strain gauge are preferably arranged in the neutral fiber of the connecting element, thus ensuring that the measurement of the bending of the connecting element is free from interference variables. The neutral fiber of a mechanical structure is free of longitudinal stresses or strains that are present in other portions of the mechanical structure during bending. Substrates of different thickness can be laminated in, so as to be able to vary the sensitivity of the sensor. The thicker the substrate, the more sensitive the sensor, since the distortions on the strain gauge are higher at a given deformation.

The substrate can be designed as a plate, e.g. a plastic or metal plate, or as a rod-shaped, in particular cylindrical or sleeve-shaped substrate. Several sensors or strain gauges can be arranged on one substrate, in particular strain gauges can be arranged on opposite sides of the substrate, so as to be able to detect bending and torsional moments free of interference. Likewise, several signal-conditioning means can be arranged on a substrate. The sensors can be arranged spaced apart from one another on the substrate, along the longitudinal extent of the substrate, and on or in the connecting element.

In one embodiment of the invention, the connecting element is designed as a heel spring, which is arranged laterally or dorsally with respect to the orthosis wearer. Particularly in the case of a heel spring arranged dorsally with respect to the orthosis wearer, provision is made that the sensor is arranged posterior to the ankle, in which case the incorrect measurement, the offset, arising from the distance to the actual ankle joint can be subtracted, such that the ankle moment can be estimated when the position is known.

The connecting element is preferably made of a fiber-reinforced composite material, for example a glass-fiber-reinforced or carbon-fiber reinforced composite material, and is designed as a beam spring element, for example.

The connecting element can be connected to the upper part and/or the lower part in an exchangeable manner, in order to ensure simple adaptation to different physiological conditions of the persons wearing the orthopedic components, for example to permit adaptation to body weight, physical ability or height. As an alternative to this, the connecting element is designed as part of the upper part and/or of the lower part, such that, for example, a foot part and a dorsal spring are designed in one piece in order to be connected in the form of a lower leg structure to the upper part. Conversely, the connecting element can be designed in one piece with the upper part, such that only the lower part has to be arranged on the connecting element. Upper part and lower part have different structures and/or functions, for example knee joint and foot or front foot and ankle, which have to be coupled. This coupling is effected via the connecting element.

The sensor can be designed to take up axial forces so as to be able to detect a compression load or tensile load inside the connecting element. If the sensor is based on strain gauge technology, one or more strain gauges can be applied in an oblique orientation with respect to the longitudinal extent of the substrate element. Depending on the desired direction of measurement of the sensor element, the sensor can also be laminated in obliquely with respect to the longitudinal extent of the connecting element.

In a design of the connecting element as a connecting part between a lower part of a knee joint and a foot part, and in a corresponding arrangement of the connecting element in the lower leg area, provision is preferably made that the sensor or the sensors is or are arranged in the area of the ankle joint in order to be able to determine the effective ankle moment as accurately as possible.

Several sensors can be arranged spaced axially apart from one another on the connecting element, in order to increase the accuracy of the detection of the effective forces and moments. In addition to the laminated-in sensor or the laminated-in sensors, at least one further sensor can be secured on the surface of the connecting element and supplies supplementary data.

In addition to signal transmission via cable, the sensor data can also be transmitted wirelessly in order to supply a corresponding control device with the required signals.

The invention also relates to an orthosis device with an upper part, which has a fastening means for securing to a thigh, a lower part, which has a fastening means for securing to a lower leg, and a foot part connected to the lower part and supporting a foot, the upper part and the lower part being connected pivotably to each other about a joint axis, and an actuator being arranged between the upper part and the lower part, and with a connecting element which is of the kind described above and which is arranged between the foot part and the lower part and connects these to each other.

Illustrative embodiments of the invention are explained in more detail below with reference to the attached figures, in which:

FIG. 2 shows a sensor on a substrate plate;

FIG. 3 shows an example of the arrangement of sensors according to FIG. 2 in a connecting element;

FIG. 4 shows a variant of the sensor according to FIGS. 2; and

FIG. 5 shows an example of the arrangement of the sensor according to FIG. 4.

Figure 1:
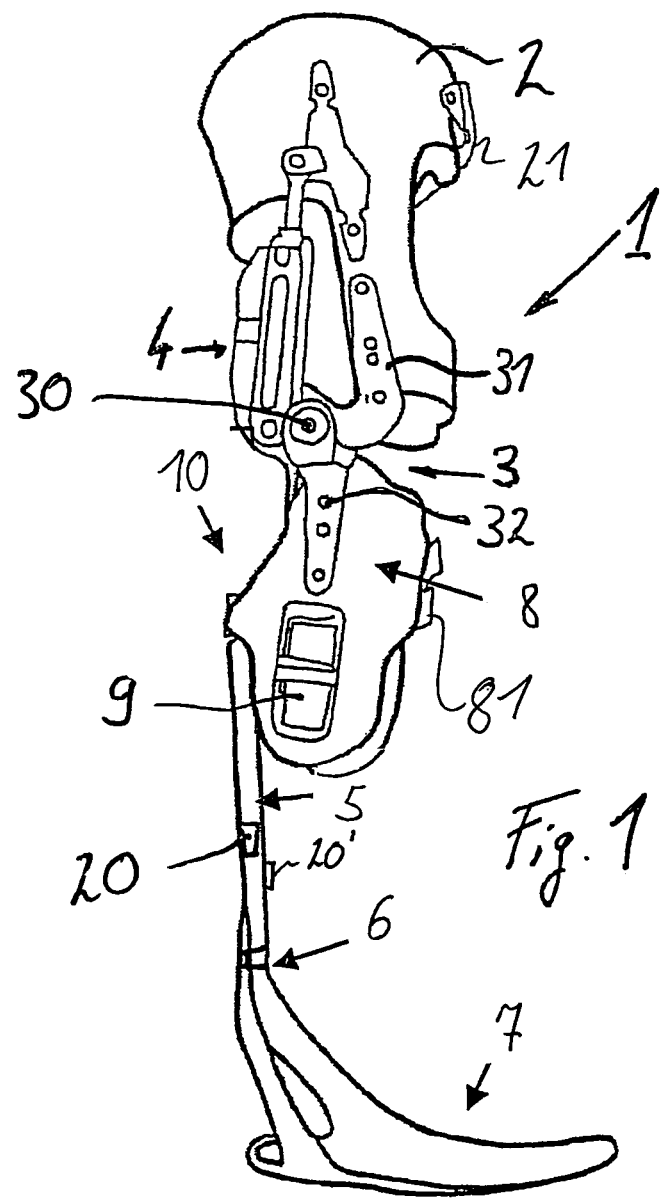
FIG. 1 shows a knee-ankle-foot orthosis in a side view.

In FIG. 1, a knee-ankle-foot orthosis 1 is shown in a side view. The orthosis 1 has a thigh structure 2, on which a joint mechanism 3 is provided for securing a lower leg structure 8 in an articulated manner. The joint mechanism 3 is secured via joint structure elements 31, 32. By means of an actuator 4, which in the present illustrative embodiment is designed as a hydraulic device that can optionally be coupled to a further actuator, the movement between the thigh structure 2 and the lower leg structure 8 can be controlled, for example by setting different degrees of damping of the movement between the thigh structure 2 and the lower leg structure 8. The lower leg structure 8 pivots relative to the thigh structure 2 about the joint axis 30, said thigh structure 2 and lower leg structure 8 being fastened to the thigh and lower leg of the orthosis wearer via fastening means 21, 81.

A foot part 7 is connected to the lower leg structure 8 via a connecting element 5, which in the present illustrative embodiment is designed as a beam spring element. The foot part 7 is secured on the connecting element 5 via an adapter 6. The foot part 7 and the adapter 6 can either be designed in one piece or be made up of several components. An adapter 10 is also provided on the lower leg structure 8 and allows the beam spring element 5 to be secured on the orthosis 1 in an exchangeable manner, the lower leg structure 8 being seen as the upper part and the foot part 7 as the lower part. For securing, the ends of the connecting element 5 are pushed into the respective adapters 6, 10 and fixed there, for example by screws. The design as clamping adapters 6, 10 is preferable, since drilling holes in fiber composite materials is, on the one hand, a difficult procedure and, on the other hand, leads to a considerable loss of strength of the fiber composite material of the connecting element 5. As an alternative to designing the connection between the connecting element 5 and the foot part 7 and lower leg structure 8 via adapters 6, 10, the connecting element 5 can also be designed in one piece with the foot part 7 and/or the lower leg structure 8.

In the illustrative embodiment shown, the connecting element 5 is arranged dorsally, but it is in principle also possible to provide such a connecting element 5 as a spring frontally, medially and/or laterally, in which case it is still possible to exchange the springs. The dorsal arrangement of the spring 5 has the advantage of achieving a very slender silhouette for the orthosis wearer, with the result that the orthosis can be worn as inconspicuously as possible. This arrangement also permits the configuration of a beam spring having the greatest possible length, which has a positive effect on the spring properties and the stability of the spring element 5.

A sensor 20 is arranged in the connecting element 5 for the purpose of determining the bending moment or other effective forces inside the connecting element 5. The sensor data can be transmitted to a control device 9, which can vary the behavior of the actuator 4. The actuator 4 can be designed as an active adjusting element, although a design as a purely passive damper is also possible, or a combination of these. An additional sensor 20' is arranged on the outside of the connecting element 5 and provides additional data concerning the effective forces and moments in the connecting element 5.

FIG. 2 is a schematic cross-sectional view showing the design of a sensor 20 with a strain gauge element 21, which is secured on a substrate 22. The strain gauge element 21 is secured in a conventional manner on the substrate 22, for example adhesively bonded, and is screened off from the environment by separating layers 23. The separating layers 23 are fixed on the substrate 22 and can be composed, for example, of a separating film, a heat-shrink sleeve or a silicone encapsulation or coating. These separating layers 23, which are arranged on the top and also on the underside of the substrate 22, avoid shearing forces being transmitted to the substrate 22 and to the strain gauge 21 secured thereon. Provided laterally alongside the separating layers 23, connection areas 24 of the substrate 22 are provided at which the substrate 22 can be connected to the surrounding composite material. These connection areas 24 come into contact with the binders of the fiber composite material and thus establish a connection to the fiber materials. In some cases, it is advantageous if the substrate 22 is not connected to the fiber composite material, since better temperature compensation can be achieved in this way. In this case, the entire sensor 20 is to be covered with a separating layer 23, thereby resulting in a floating arrangement inside the fiber composite material.

FIG. 3 is a schematic side view of the connecting element 5 in the form of a beam spring element, for example. A sensor 20 with a screened-off strain gauge 21 on a substrate 22 is laminated in on each side of the neutral fiber 55. Cables 25, which are connected to the strain gauge 21, lead from the connecting element 5 to amplifying and signal-conditioning electronics, which can likewise be laminated in, and optionally to a control device. The substrate 22 is preferably thin, for example between 0.1 mm and 0.5 mm, such that the whole arrangement of the sensor 20 with the strain gauges 21 and separating layers 23 has a thickness of less than 1 mm. The sensitivity of the sensors can be adjusted by the position inside the connecting element 5, the change arising from the variation in the distance from the neutral fiber 55. As clearly shown in FIG. 3, the sensor 20, being positioned inside of the laminate structure, is isolated.

FIGS. 4 and 5 show a variant of the invention in which strain gauges 21 are arranged on both sides of the substrate 22 and are surrounded by separating layers 23. Here too, connection areas 24 are provided alongside the separating layers 23 in order to be laminated into the connecting element 5. However, the connection areas 24 are not absolutely essential. FIG. 5 is a sectional view showing the arrangement of the sensor 20 according to FIG. 4 inside the connecting element 5. The sensor 20 is arranged in the neutral fiber 55 of the connecting element 5, and the cables 25 lead from the connecting element 5. The substrate 22 bends together with the connecting element 5 and generates an output signal. Because the strain gauges 21 are arranged directly adjacent to the neutral fiber 55, a relatively high amplification factor is needed in order to achieve the necessary sensitivity of the sensor. However, the sensitivity can also be varied by the thickness of the substrate 22. In the design of the sensor unit, a compromise has to be found between sensitivity, thickness of the sensor and amplification factor. However, there is the advantage that only a single foreign body has to be arranged inside the composite material element 5. This foreign body in the form of the sensor 20, if appropriate together with the amplification and evaluation electronics, can be easily inserted and laminated in as a completely prefabricated module.

The invention claimed is:

1. A connecting element between two rigidly coupled orthopedic components, in particular orthosis components, with an upper part and a lower part, the connecting element comprising:
   a laminate material having a laminate structure, including a neutral fiber, the neutral fiber being free of longitudinal stresses or strains during bending of the connecting element;
   at least one sensor to determine a bending moment or another effective force inside the connecting element, the at least one sensor being embedded inside the laminate structure of the connecting element during formation of the connecting element, the at least one sensor being positioned inside the connecting element to isolate the at least one sensor, the at least one sensor being arranged adjacent to the neutral fiber, the at least one sensor being designed as a strain gauge, which is arranged on a substrate;
   a separating layer arranged between the at least one sensor and the laminate material, the separating layer being secured on the substrate.

2. The connecting element as claimed in claim 1, wherein the at least one sensor is laminated inside the connecting element.

3. The connecting element as claimed in claim 1, wherein the at least one sensor is screened off from shearing forces of the laminate material.

4. The connecting element as claimed in claim 1, wherein the strain gauge is arranged on a circuit board, which serves as substrate, of evaluation electronics.

5. The connecting element as claimed in claim 1, wherein the strain gauge is designed in thick-film technology.

6. The connecting element as claimed in claim 1, wherein the substrate is laminated in the connecting element in such a way that it follows deformations formed in the connecting element.

7. The connecting element as claimed in claim 1, wherein the substrate is designed as a plate.

8. The connecting element as claimed in claim 1, wherein the substrate is arranged floating in the connecting element.

9. The connecting element as claimed in claim 1, wherein the at least one sensor includes several sensors, which are arranged on one substrate.

10. The connecting element as claimed in claim 1, wherein the substrate includes a plurality of substrates of different thickness, which are laminated in the connecting element.

11. The connecting element as claimed in claim 1, wherein the connecting element is designed as a heel spring, which is adapted to be arranged laterally or dorsally with respect to an orthosis wearer.

12. The connecting element as claimed in claim 1, wherein the connecting element is made of a fiber-reinforced composite material.

13. The connecting element as claimed in claim 1, wherein the connecting element is connected to the upper part and/or the lower part in an exchangeable manner.

14. The connecting element as claimed in claim 1, wherein the connecting element is designed in one piece with the upper part and/or the lower part.

15. The connecting element as claimed in claim 1, wherein the at least one sensor is designed as a bending moment or torsional moment sensor.

16. The connecting element as claimed in claim 1, wherein the at least one sensor can detect axial forces.

17. The connecting element as claimed in claim 1, wherein the at least one sensor is designed as a strain gauge and is laminated in an oblique orientation with respect to the longitudinal extent of the connecting element.

18. The connecting element as claimed in claim 1, wherein the connecting element is adapted to be arranged in the lower leg area, and the at least one sensor is adapted to be arranged in an area of an ankle joint.

19. The connecting element as claimed in claim 1, wherein the at least one sensor includes several sensors, which are arranged spaced axially apart from one another on the connecting element.

20. The connecting element as claimed in claim 1, wherein at least one further sensor is arranged on an exterior surface of the connecting element.

21. An orthosis device, comprising:
   an upper part, which has a fastener for securing to a thigh;
   a lower part, which has a fastener for securing to a lower leg;
   a foot part connected to the lower part and supporting a foot, the upper part and the lower part being connected pivotably to each other about a joint axis;
   an actuator being arranged between the upper part and the lower part;
   a connecting element being arranged between and connecting the foot part and the lower part, the connecting element comprising:
      a laminate material having a laminate structure, including a neutral fiber, the neutral fiber being free of longitudinal stresses or strains during bending of the connecting element;
      at least one sensor to determine a bending moment or another effective force inside the connecting element, the at least one sensor being embedded inside the laminate structure of the connecting element during formation of the connecting element, the at least one sensor being positioned inside the connecting element to isolate the at least one sensor, the at least one sensor being arranged adjacent to the neutral fiber, the at least one sensor being designed as a strain gauge, which is arranged on a substrate;
      a separating layer arranged between the at least one sensor and the laminate material, the separating layer being secured on the substrate.

22. A connecting element for use between an upper part and a lower part of an orthopedic device, the connecting element comprising:
   a laminate structure having a plurality of fiber layers, including a neutral fiber, the neutral fiber being free of longitudinal stresses or strains during bending of the connecting element;
   at least one sensor positioned inside the laminate structure adjacent to the neutral fiber between the plurality of fiber layers during formation of the connecting element, the at least one sensor being configured to determine a bending moment or other effective force inside the connecting element, the at least one sensor being designed as a strain gauge, which is arranged on a substrate;
   a separating layer arranged between the at least one sensor and the laminate structure, the separating layer being secured on the substrate.

23. A connecting element between two rigidly coupled orthopedic components, in particular orthosis components, with an upper part and a lower part, wherein the connecting element comprises:
   a laminate material having a laminate structure, including a neutral fiber, the neutral fiber being free of longitudinal stresses or strains during bending of the connecting element;
   at least one sensor to determine a bending moment or another effective force inside the connecting element, the at least one sensor being embedded inside the laminate structure adjacent to the neutral fiber during formation of the connecting element, the at least one sensor being positioned inside the connecting element to isolate the at least one sensor; the at least one sensor being designed as a strain gauge, the strain gauge being arranged on a circuit board, the circuit board serving as a substrate for evaluation electronics;
   a separating layer arranged between the at least one sensor and the laminate material, the separating layer being secured on the substrate.

* * * * *